United States Patent

Mashiba et al.

Patent Number: 5,212,323
Date of Patent: May 18, 1993

[54] PROCESS FOR PRODUCING 6-(3-DIMETHYLAMINOPROPIONYL)FORSKOLIN

[75] Inventors: Akihiro Mashiba, Tokyo; Yutaka Ogawa, Saitama, both of Japan

[73] Assignee: Nippon Kayaku Kabushiki Kaisha, Tokyo, Japan

[21] Appl. No.: 781,979

[22] Filed: Oct. 24, 1991

[30] Foreign Application Priority Data

Nov. 1, 1990 [JP] Japan .................... 2-293679

[51] Int. Cl.$^5$ .......................................... C07D 311/92
[52] U.S. Cl. .................................................. 549/389
[58] Field of Search ......................................... 549/389

[56] References Cited

FOREIGN PATENT DOCUMENTS 0297496  1/1989  European Pat. Off. .

Primary Examiner—Nicky Chan
Attorney, Agent, or Firm—Nields & Lemack

[57] ABSTRACT

Disclosed in a process for producing 6-(3-dimethylaminopropionyl)forskolin, comprising the sequential steps of:

(1) acetylating hydroxy groups in the 1-position and 7-position of a compound represented by the formula (III):

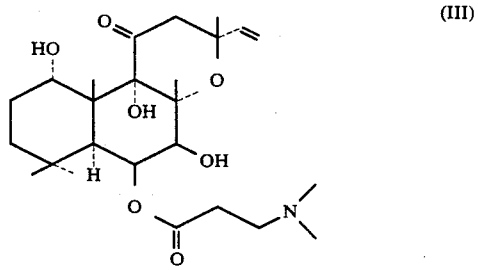

to prepare 1-acetyl-6-(3-dimethylaminopropionyl)-forskolin represented by the formula (II):

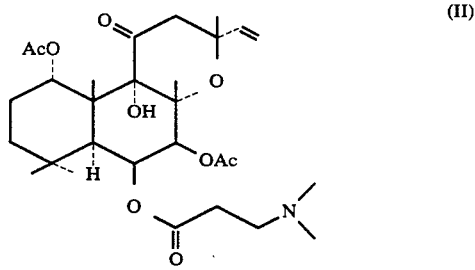

(wherein Ac represents acetyl group), and (2) selectively removing the acetyl group in the 1-position of the compound represented by the formula (II) in the presence of an amine represented by the formula (IV):

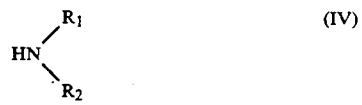

(wherein $R_1$ represents hydrogen atom or lower alkyl group having 1-6 carbon atoms, and $R_2$ represents lower alkyl group having 1-6 carbon atoms, alkoxyalkyl group, aminoalkyl group or benzyl group) in a solvent to prepare 6-(3-dimethylaminopropionyl)forskolin represented by the formula (I):

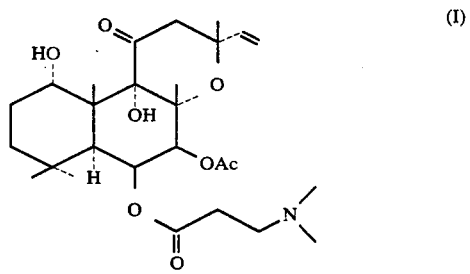

(wherein Ac represents the same as defined in the formula (II)).

The compound (I) is promising as a therapeutic agent for cardiac failure.

7 Claims, No Drawings

PROCESS FOR PRODUCING 6-(3-DIMETHYLAMINOPROPIONYL)FORSKOLIN

BACKGROUND OF THE INVENTION

1. Field of the Invention

The present invention relates to a novel process for producing 6-(3-dimethylaminopropionyl)-forskolin promising as a therapeutic agent for cardiac failure.

2. Description of the Prior Art

A process, wherein hydroxy groups in the 1-position and 7-position of a compound represented by a formula (III) shown below are acetylated to prepare a compound represented by a formula (II) shown below and then the acetyl group in the 1-position of the compound represented by the formula (II) is selectively removed to prepare 6-(3-dimethylaminopropionyl)forskolin represented by a formula (I) shown below, is already known in the art (EP-0297496-A2).

According to the above-described EP patent specification, the yield of the compound represented by the formula (I) is 54% by weight based on the weight of the compound represented by the formula (III), using sodium hydroxide as a deacetylating agent. It has been desired to increase the yield.

SUMMARY OF THE INVENTION

The present inventors have made various studies and, as a result, have found that the use of an amine represented by the formula (IV):

(IV)

(wherein $R_1$ represents hydrogen atom or lower ($C_1$-$C_6$) alkyl group, and $R_2$ represents lower ($C_1$-$C_6$) alkyl group, alkoxyalkyl group, aminoalkyl group or benzyl group) as a deacetylating agent enables the compound represented by the formula (I) to be prepared with a high purity and in a high yield of about 90%.

The present invention has been accomplished based on the above finding.

That is, the present invention provides a process for producing 6-(3-dimethylaminopropionyl)-forskolin, comprising the sequential steps of: (1) acetylating hydroxy groups in 1-position and 7-position of a compound represented by the formula (III):

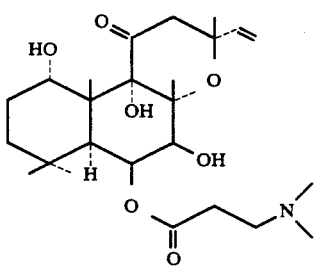
(III)

to prepare 1-acetyl-6-(3-dimethylaminopropionyl)-forskolin represented by the formula (II):

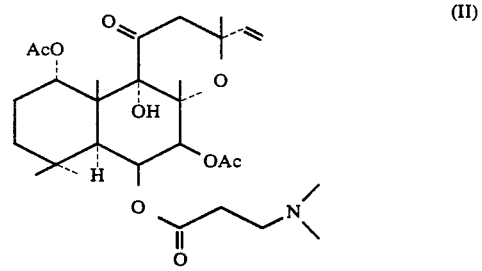
(II)

(wherein Ac represents acetyl group), and (2) selectively removing the acetyl group in the 1-position of the compound represented by the formula (II) in the presence of an amine represented by the formula (IV):

(IV)

(wherein $R_1$ represents hydrogen atom or lower alkyl group having 1-6 carbon atoms, and $R_2$ represents lower alkyl group having 1-6 carbon atoms, alkoxyalkyl group, aminoalkyl group or benzyl group) in a solvent to prepare 6-(3-dimethylaminopropionyl)forskolin represented by the formula (I):

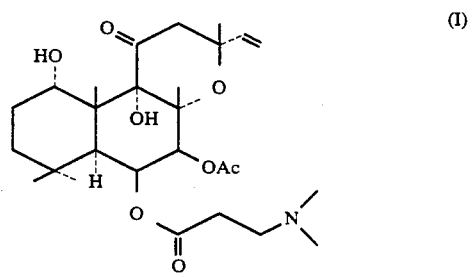
(I)

(wherein Ac represents the same as defined in the formula (II)).

According to the process of the present invention, it is possible to quantitatively produce 6-(3-dimethylaminopropionyl)forskolin as an intended product with a high purity through complete prevention of the decomposition of the product into a by-product unattainable by the prior art. This enables 6-(3-dimethylaminopropionyl)forskolin having a high quality to be produced in a high yield through mere separation after the reaction without troublesome purification procedure such as column chromatography and recrystallization from a solvent, which renders the process of the present invention suitable for synthesis on a large scale.

DETAILED DESCRIPTION OF THE INVENTION $R_1$ in the amine represented by the formula (IV) described above includes hydrogen atom and lower ($C_1$-$C_6$) alkyl group such as methyl, ethyl, propyl, butyl, pentyl and hexyl. $R_2$ includes the same as lower $C_1$-$C_6$ alkyl group in $R_1$; alkoxyalkyl group such as methoxypropyl and ethoxypropyl; aminoalkyl group such as aminoethyl, methylaminopropyl and dimethylaminopropyl; phenyl group; and the like.

Examples of the amine represented by the formula (IV) includes dimethylamine, diethylamine, di-n-propylamine, diisopropylamine, di-n-butylamine, diisobutylamine, methylamine, ethylamine, n-propylamine, isopropylamine, n-butylamine, isobutylamine, sec-butylamine, tert-butylamine, n-pentylamine, n-hexylamine, cyclohexylamine, 3-methoxypropylamine, 3-ethoxypropylamine, 2-ethylhexylethoxypropylamine, ethylenediamine, methylaminopropylamine, dimethylaminopropylamine, diethylaminopropylamine, benzylamine and so on. The most preferable amine is dimethylamine in view of prevention of by-products from being produced by an exchange reaction which exchanges dimethylamino group in dimethylaminopropyonyl group in 6-position of the compound represented by the formula (I) with other amino groups.

The amine used in the present invention may be in the form of either a solution or a gas. When the amine is in the form of a solution, water is preferred as a solvent. Although there is no particular limitation on the amount of use of the amine as far as the amount is 0.1 equivalent or more based on 1-acetyl-6-(3-dimethylaminopropionyl)forskolin represented by the formula (II) or the compound represented by the formula (III), the amount is preferably 0.1 to 20 equivalents, more preferably 1.0 to 20 equivalents.

There is no particular limitation on the reaction solvent used in the present invention as far as it dissolves 1-acetyl-6-(3-dimethylaminopropionyl)-forskolin represented by the formula (II) and is not detrimental to the reaction, and generally, polar solvent is used. The preferable solvent is $C_1$-$C_4$ organic polar solvent and examples of the solvent include alcohols such as methanol, ethanol and propanol; ketones such as acetone and methyl ethyl ketone; esters such as methyl acetate and ethyl acetate; halogenated hydrocarbons such as methylene chloride and chloroform; dimethyl sulfoxide; N,N-dimethylformamide and hydrous solvents comprising the above-mentioned solvents in the case of solvents miscible with water.

The hydrous solvent contains water in an amount of preferably 50 v/v% or less, more preferably 0.5–40 v/v%. A further preferred hydrous solvent is an alcohol which has 1-4 carbon atoms and contains water in an amount of 0.5–20 v/v%.

The reaction temperature is usually in the range of from 0° C. to the boiling point of the solvent, preferably from 0° C. to 80° C, more preferably from 15° C. to 50° C., and the reaction is completed in 4 to 40 hr. When reaction temperature is low, reaction time become long. However, the reaction time can be shortened by raising the reaction temperature on the way.

When the reaction solvent is a solvent miscible with water, the intended product can be readily isolated from the reaction mixture by adding water to the reaction mixture after the completion of the reaction in the same amount as that of the solvent or preferably in such an amount as to afford a 40 to 60 v/v% hydrous solvent, and then filtering the mixture.

When the reaction solvent is not miscible with water, the separation can be conducted by adding water to the reaction mixture, separating the resultant organic phase, concentrating the organic phase, adding a hydrous alcohol to the residue for crystallization and collecting the formed crystals by filtration. In this case, washing the crystals with a hydrous alcohol is more effective.

As described in EP-027496-A2 above, the compound (II) is prepared by acetylating hydroxyl groups in 1-position and 7-position of the compound (III) with acetylating agent in a solvent. That is to say, the acetylation of the compound of the formula (III) is carried out by the use of about 2 to about 50 mol, preferably about 2 to about 4 mol of an acetylating agent per mol of the compound (III) in a solvent at a temperature of about 0° C. to a boiling point of the solvent, preferably about 0° C. to 35° C. for several minutes to about 24 hours, preferably several minutes to about 2 hours. Examples of the solvent to be used in the acetylation include pyridine, benzene, chloroform, ether, dichloromethane, 1,1,1-trichloroethane, 1,2-dichloroethane, carbon tetrachloride and ethyl acetate, preferably pyridine.

The acetylating agent includes acetic acid and reactive derivatives thereof such as acetyl halide (acetyl chloride, acetyl bromide, etc.), acetic anhydride, and so on. In this reaction, using of catalytic amount of 4-dimethylaminopyridine is preferable because the reaction goes on smoothly without high reaction temperature.

The compound (II) obtained by the above acetylation reaction is used after the solvent is distilled away. The thus obtained crude product per se may be used in the following selective deacetylation reaction. However, it is preferable that acid components such as acetic acid be removed from the crude product. In order to remove the acid components, for example, a method can be employed in which the crude product is dissolved in a water-immiscible organic solvent containing an alkali such as ammonia and then water is added thereto to extract the acid components with water.

The present invention will now be described in more detail with reference to the following Examples.

EXAMPLE 1

(1-1) 6.55 g (64.14 mmol) of acetic anhydride was added to a mixed solution comprising 10.0 g (21.38 mmol) of 7-deacetyl-6-(3-dimethylaminopropionyl)forskolin, 7.0 mg of 4-dimethylaminopyridine and 30 ml of pyridine with ice cooling. After a reaction was allowed to proceed at 20° C. for 5 hr, 3 ml of methanol was added to the reaction mixture, and the mixture was concentrated under reduced pressure to remove the solvent.

After 80 ml of ethyl acetate, 8 g of concentrated aqueous ammonia and 20 ml of 10% saline solution were added to the residue, the mixture was stirred and then allowed to stand, and the resultant organic phase was separated. The organic phase was washed twice with 20 ml of 10% saline solution and then dried over anhydrous magnesium sulfate. The resultant solid matter was removed by filtration, and the filtrate was concentrated under reduced pressure to give oily 1-acetyl-6-(3-dimethylaminopropionyl)forskolin.

(1-2) To the residue were added 30 ml of methanol and 3.9 g (42.76 mmol) of a 50% aqueous dimethylamine solution, and a reaction was allowed to proceed at room temperature for 20 hr. After the completion of the reaction, 30 ml of water was added to the reaction mixture to precipitate crystals.

The crystals were collected by filtration, washed with 10 ml of 50% methanol and dried to give 9.8 g of 6-(3-dimethylaminopropionyl)forskolin [yield: 90% based on 7-deacetyl-6-(3-dimethylaminopropionyl)-forskolin].

The NMR and IR spectra of the product were in complete agreement with those of a separately synthesized standard sample.

Incidentally, the compound (I) can also be obtained by using methylamine, ethylenediamine, 3-methoxypropylamine or benzylamine instead of dimethylamine in example 1-2 above.

EXAMPLE 2

To oily 1-acetyl-6-(3-dimethylaminopropionyl)-forskolin prepared in a similar manner to that of Example 1-1 were added 30 ml of methanol, 20 ml of water and 7.8 g (85.5 mmol) of a 50% aqueous dimethylamine solution, and a reaction was allowed to proceed at 40° to 45° C. for 5 hr.

After the completion of the reaction, the reaction mixture was cooled to room temperature and the precipitated crystals were collected by filtration, washed with 10 ml of 50% methanol, and dried to give 9.9 g of 6-(3-dimethylaminopropionyl)forskolin [yield: 91% based on 7-deacetyl-6-(3-dimethylaminopropionyl)-forskolin].

The NMR and IR spectra of the product were in complete agreement with those of a separately synthesized standard sample.

EXAMPLE 3

To oily 1-acetyl-6-(3-dimethylaminopropionyl)-forskolin prepared in a similar manner to that of Example 1-1 were added 30 ml of ethyl acetate and 29 g (0.32 mol) of a 50% aqueous dimethylamine solution, and a reaction was allowed to proceed at room temperature for 24 hr.

After the completion of the reaction, the solvent was removed by distillation under reduced pressure and 30 ml of ethyl acetate and 10 ml of water were added to the residue. The mixture was stirred and then allowed to stand, and the resultant organic phase was separated. After the organic phase was dried over anhydrous magnesium sulfate, the solid matter was removed by filtration, and the filtrate was concentrated and evaporated to dryness under reduced pressure.

30 ml of methanol and 30 ml of water were added to the resultant residue for crystallization, and the formed crystals were collected by filtration, washed with 20 ml of water and dried to give 9.6 g of 6-(3-dimethylaminopropionyl)forskolin [yield: 88% based on 7-deacetyl-6-(3-dimethylaminopropionyl)forskolin].

The NMR and IR spectra of the product were in complete agreement with those of a separately synthesized standard sample.

The following is another example of acetylation of the compound (III):

A mixture comprising 12 g of 7-deacetyl-6-(3-dimethylaminopropionyl)forskolin, 35 mg of 4-dimethylaminopyridine, 48 ml of anhydrous pyridine and 5.9 ml of acetic anhydride was stirred at room temperature for 2 hours, followed by the addition of 35 mg of 4-dimethylaminopyridine. The mixture was further stirred for 3 hours. After the completion of the reaction, 5 ml of methanol was added to the reaction mixture and the mixture was concentrated.

What is claimed is:

1. A process for producing 6-(3-dimethylamino-propionyl)forskolin, comprising the sequential steps of:
   (1) acetylating hydroxy groups in 1-position and 7-position of a compound represented by the formula (III):

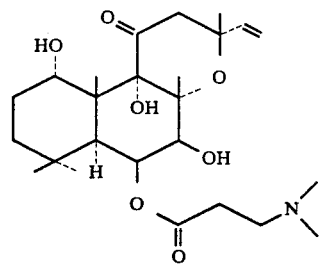

to prepare 1-acetyl-6-(3-dimethylaminopropionyl)-forskolin represented by the formula (II):

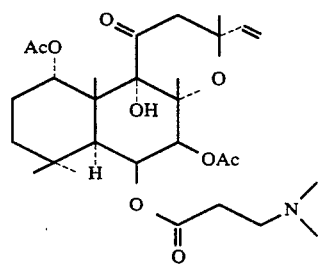

(wherein Ac represents acetyl group), and
(2) selectively removing the acetyl group in the 1-position of the compound represented by the formula (II) while avoiding the formation of by-products, consisting essentially of reacting the compound represented by the formula (II) with dimethylamine in a group solvent to prepare 6-(3-dimethylaminopropionyl)forskolin represented by the formula (I):

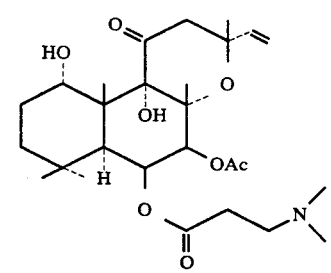

(wherein Ac represents the same as defined in formula (II)).

2. A process according to claim 1, wherein the dimethylamine is used in an amount of 0.1-20 equivalents based on the compound represented by the formula (II).

3. A process according to claim 1, wherein the solvent is an alcohol or an ester.

4. A process according to claim 1, wherein the solvent is methanol.

5. A process according to claim 1, wherein the acetyl group is removed at 0° C. to 80° C. in the step (2).

6. A process for producing 6-(3-dimethylaminopropionyl)forskolin, comprising the sequential steps of:
   (1) treating a compound represented by the formula (III):

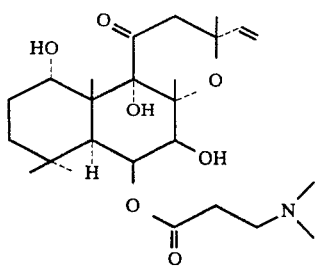

with 2-8 mol of an acetylating agent in the presence of 4-dimthylaminopyridine in pyridine per mol of the compound represented by the formula (III) to prepare 1-acetyl-6-(3-dimethylaminopropionyl)forskolin represented by the formula (II):

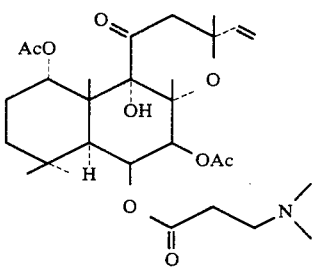

(wherein Ac represents acetyl group), and (2) removing the acetyl group in the 1-position of the compound represented by the formula (II) while avoiding the formation of by-products in the presence of 0.1-20 mol of dimethylamine in methanol per mol of the compound represented by the formula (III) to prepare 6-(3-dimethylaminopropionyl)forskolin represented by the formula (I):

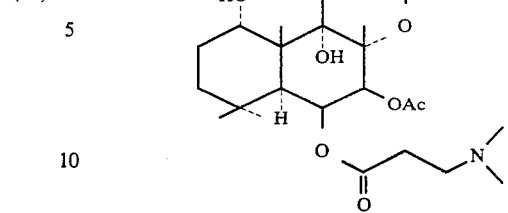

(wherein Ac represents the same as defined in the formula (II)).

7. A process for producing 6-(3-dimethylaminopropionyl)forskolin represented by the formula (I):

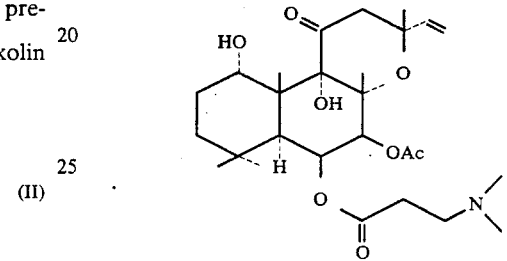

(wherein Ac represents an acetyl group), the process comprising the step of removing an acetyl group in 1-position of 1-acetyl-6-(3-dimethylaminopropionyl)-forskolin represented by the formula (II):

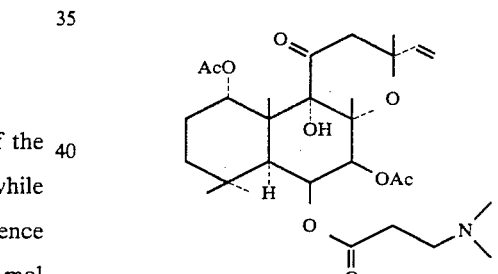

(wherein Ac is as defined above) while avoiding the formation of by-products, in the presence of dimethylamine in a solvent.

* * * * *